(12) United States Patent
Håkansson et al.

(10) Patent No.: US 8,110,347 B2
(45) Date of Patent: Feb. 7, 2012

(54) DIAGNOSTIC METHOD FOR DETECTING CANCER BY MEASURING AMOUNT OF CYTOKINE LIKE IL-6

(75) Inventors: Leif Håkansson, Höllviken (SE); Birgitta Clinchy, Ljungsbro (SE); Rune Sjödahl, Linköping (SE)

(73) Assignee: Canimguide Therapeutics AB, Höllviken (SE)

( * ) Notice: Subject to any disclaimer, the term of this patent is extended or adjusted under 35 U.S.C. 154(b) by 332 days.

(21) Appl. No.: 11/918,488

(22) PCT Filed: Apr. 12, 2006

(86) PCT No.: PCT/SE2006/000440
§ 371 (c)(1),
(2), (4) Date: May 29, 2008

(87) PCT Pub. No.: WO2006/110091
PCT Pub. Date: Oct. 19, 2006

(65) Prior Publication Data
US 2009/0081649 A1 Mar. 26, 2009

(30) Foreign Application Priority Data

Apr. 15, 2005 (SE) ...................................... 0500889
Nov. 4, 2005 (SE) ...................................... 0502506

(51) Int. Cl.
*C12Q 1/00* (2006.01)
(52) U.S. Cl. ........................................................... 435/4
(58) Field of Classification Search .................... None
See application file for complete search history.

(56) References Cited

U.S. PATENT DOCUMENTS

| 5,284,750 A | 2/1994 | Silvestrini et al. |
| 6,737,057 B1 | 5/2004 | Zaghouani |
| 2003/0021792 A1 | 1/2003 | Roben et al. |
| 2005/0153329 A1 | 7/2005 | Hakansson et al. |

FOREIGN PATENT DOCUMENTS

| JP | 62-016430 | 1/1987 |
| JP | 2005089325 | 4/2005 |
| WO | WO 91/09619 | 7/1991 |
| WO | WO 00/28072 | 5/2000 |
| WO | WO 02/30465 | 4/2002 |
| WO | WO 03/099312 A1 * | 12/2003 |
| WO | WO 2004/048933 | 6/2004 |
| WO | WO 2006/043891 | 4/2006 |
| WO | WO 2006/110091 | 10/2006 |
| WO | WO 2008/136736 | 11/2008 |

OTHER PUBLICATIONS

Wu et al (Am J Gastroenterol, 1996, 91(7): Abstract).*
Dranchenberg et al (Prostate, 1999, 41(2):127-133).*
Belluco et al (Ann Surg Oncol, 2000, 7(2): Abstract).*
Wood et al (Br J Surg, 1980, 67(1): Abstract).*
Wu et al (Am J Gastroenterol, 1996, 91(7): 1417-1422).*
Tockman et al (Cancer Res., 1992, 52:2711s-2718s).*
Bajpai, et al., "Immunomodulating Activity of Analogs of Noninflammatory Fragment 163-171 of Human Interleukin-1 B", Immunopathology, 1998, 38:237-245.
Bhol, et al., "The autoantibodies to alpha 6 beta 4 integrin of patients affected by ocular cicatricial pemphigoid recognize predominantly epitopes within the large cytoplasmic domain of human beta 4." J. Immunol. Sep. 1, 2000;165(5):2824-9.
Brevig, et al., "The recognition of adsorbed and denatured proteins of different topographies by beta2 integrins and effects on leukocyte adhesion and activation." Bismaterials. Jun. 2005;26(16):3039-53.
Clinchy, et al., "Preoperatvie interleukin-6 production by mononuclear blood cells predicts survival after radical surgery for colorectal carcinoma." Cancer. May 1, 2007;109(9):1742-9.
Gruel, et al., "Bypassing tumor-specific and bispecific antiboides: triggering of antitumor immunity by expression of anti-FcγR scFv on cancer cell surface" *Gene Therapy* (2001) 8: 1721-1728.
Hauptman, et al., "Antibodies to human albumin in cirrhotic sera." J. Clin Invest. Jul. 1974;54(1):122-7.
Kuntz, "Structure-based strategies for drug design and discovery." Science. 1992 257(5073):1078-1082.
Miller, et al., "Ligand binding to proteins: the binding landscape model." Protein Sci. Oct. 1997;6(10):2166-79.
Oyama, et al., "Autoantibodies to extracellular matrix protein 1 in lichen sclerosus." Lancet. Jul. 12, 2003;362(9378):118-23.
Piancatelli, et al., "Local Expression of Cytokines in Human Colorectal Carcinoma: Evidence of Specific Interleukin-6 Gene Expression", Journal of Immunotherapy, 1999, vol. 22, p. 25-32.
Rouard, et al, "Fc Receptors as Targets for Immunotherapy" *Intern. Rev. Immunol.* (1997) 16: 147-185.
Ruka, et al., "Alterations of routine blood tests in adult patients with soft tissue sarcomas: Relationships to cytokine serum levels and prognostic significance" *Annals of Oncology* (2001) 12: 1423-1432.
Siedlar, et al., "Depressed Tumor Necrosis Factor Alpha and Interleukin-12p40 Production by Peripheral Blood Mononuclear Cells of Gastric Cancer Patients: Associate with IL-IR-Associated Kinase-1 Protein Expression and Disease State", Internation Journal Cancer, 2005, vol. 114, p. 144-152.

(Continued)

*Primary Examiner* — Sean Aeder
(74) *Attorney, Agent, or Firm* — Knobbe Martens Olson & Bear LLP

(57) ABSTRACT

The present invention relates to a diagnostic method for predicting the possible recurrence of tumors in cancer patients. The method comprises culturing blood cells from a patient suffering from cancer in the presence of a cytokine stimulating factor, where after the amount of induced cytokine thereby produced is determined giving an indication of the risk of recurrence of the cancer.

7 Claims, 3 Drawing Sheets

OTHER PUBLICATIONS

Figure 1:
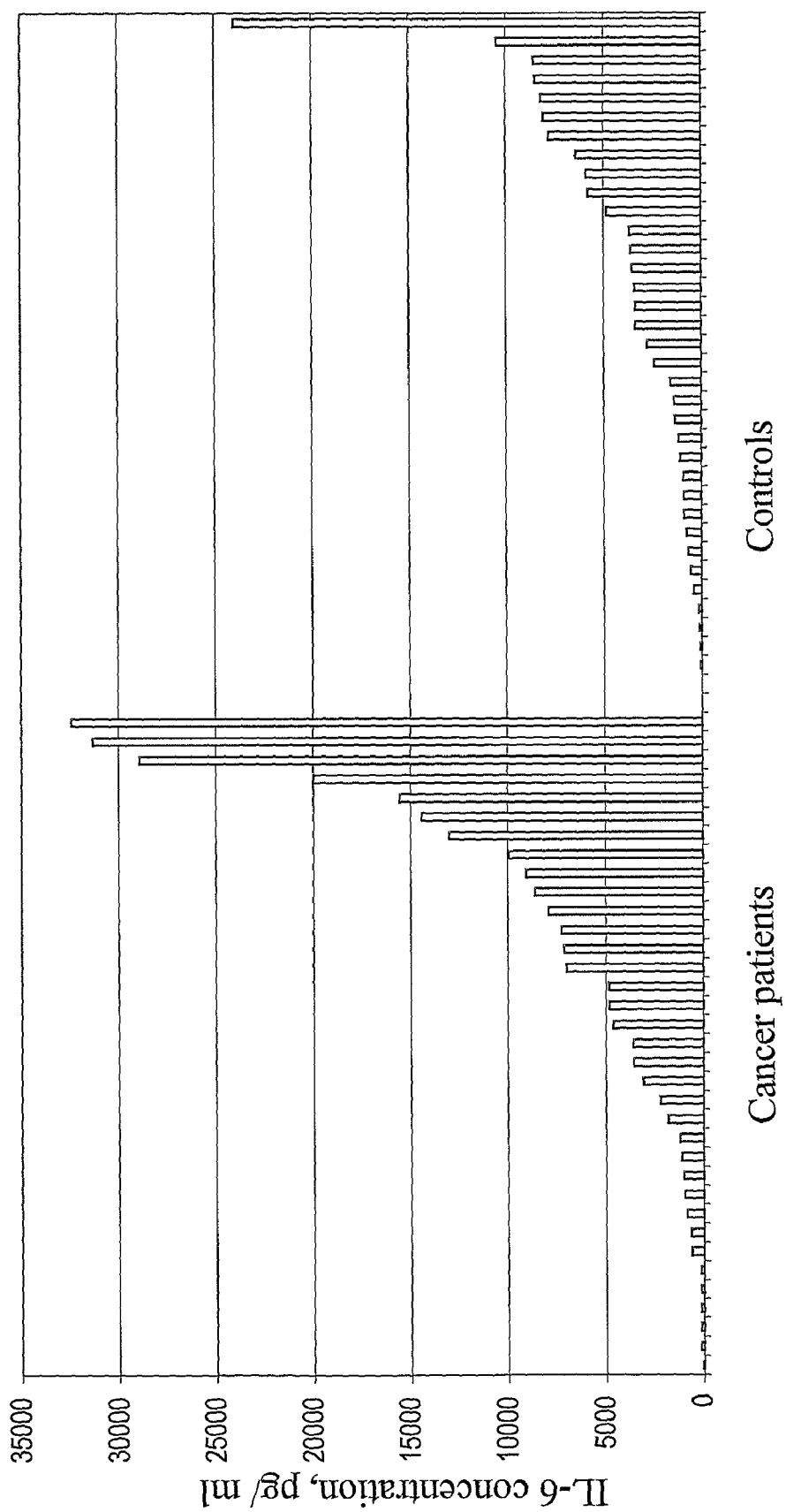

Tamura, et al., "Anti-albumin antibodies in sera of patients with liver disease." Gastroenterol Jpn. Oct. 1982;17(5):469-75.

International Search Report, dated Nov. 4, 2003, issued in PCT/SE03/00869.

International Search Report, dated Feb. 6, 2006, issued in PCT/SE05/001582.

International Search Report, dated Jul. 13, 2006, issued in PCT/SE06/000440.

International Preliminary Report on Patentability, date Dec. 4, 2006, issued in PCT/SE06/000440.

International Search Report, dated Jan. 5, 2009, issued in PCT/SE08/000314.

Belluco, Claudio et al., "Interleukin-6 Blood Level is Associate With Circulating Carcinoembryonic Antigen and Prognosis in Patients With Colorectal Cancer" Annals of Surgical Oncology, 2000, pp. 133-138, vol. 7, No. 1.

Chung, Yuan-Chang et al., "Serum Interleukin-6 Levels Reflect the Disease Status of Colorectal Canceer" Journal of Curgical Oncology, 2003, pp. 222-226, vol. 83.

Galizia, Gennaro et al., "Prognostic Significance of Circulating IL-10 and IL-6 Serum Levels in Colon Cancer Patients Undergoing Surgery" Clinical Immunology, Feb. 2002, pp. 169-178, vol. 102, No. 2.

Kaminska, Janina et al., "CRP, TNFα, IL-1ra, IL-6, IL-8 and IL-10 in Blood Serum of Colorectal Cancer Patients" Pathology Oncology Research, 2000, pp. 38-41, vol. 6, No. 1.

Kaminska, J. et al., "Clinical Significance of Serum Cytokine Measurements in Untreated Colorectal Cancer Patients: Soluble Tumor Necrosis Factor Receptor Type I—An Independent Prognostic Factor" Tumor Biology, 2005, pp. 186-194, vol. 26.

Kinoshita, Tsuneki et al., "Serum Interleukin-6 Level Reflects the Tumor Proliferative Activity in Patients with Colorectal Carcinoma" Cancer, Jun. 15, 2009, pp. 2526-2531, vol. 85, No. 12.

Nikiteas, Nikolaos I. et al., "Serum IL-6, TNFα and CRP levels in Greek colorectal cancer patients: Prognostic implications" World Journal of Gastroenterology, 2005, pp. 1639-1643, vol. 11.

Rich, Tyvin et al., "Elevated Serum Cytokines Correlated with Altered Behavior, Serum Cortisol Rhythm, and Dampened 24-Hour Rest-Activity Patterns in Patients with Metastatic Colorectal Cancer" Clinical Cancer Research, Mar. 1, 2005, pp. 1757-1764, vol. 11.

Ueda, Takashi et al., "Serum levels of cytokines in patients with colorectal cancer: Possible involvement of interleukin-6 and interleukin-8 in hematogenous metastasis", (1994).

* cited by examiner

DIAGNOSTIC METHOD FOR DETECTING CANCER BY MEASURING AMOUNT OF CYTOKINE LIKE IL-6

TECHNICAL FIELD

The present invention relates to a diagnostic method for predicting the possible recurrence of malignant tumours in cancer patients.

BACKGROUND OF THE INVENTION

Recurrence of a cancer is a serious event, in particular the appearance of distant metastases, which can no longer be resected. The cure rate of patients in this situation is generally very poor. Patients with a high risk of recurrent disease are therefore given adjuvant treatment already after radical surgery, although the existence of remaining tumour cells cannot be diagnosed at this stage. Thus, there is a great need for a method to diagnose these patients, in order to be able to give them an adequate treatment from the very beginning of the post-surgical period.

Several factors of prognostic significance for colorectal cancer (CRC) have been identified. Dukes' classification or staging based on the TNM classification gives good prognostic information, but still there is a great need for tests giving more detailed prognostic information especially for patients with Dukes' B and C or stage II and III cancers. Therefore the prognostic value of several molecular and genetic factors has been investigated. So far no single parameter, which allows individual monitoring of CRC patients, has been described. Cancer is often associated with a systemic chronic inflammation resulting in production of cytokines e.g. interleukin-6 (IL-6) and TNF-α and induction of acute phase reactants, such as C-reactive protein (CRP). High serum levels of CRP has been reported to correlate to poor prognosis, but still a fairly high recurrence rate is found in patients with normal serum levels of CRP, thus reducing the value of this parameter for individual monitoring of cancer patients. Therefore, scores based on several parameters, e.g. serum level of CRP and TNM-stage has been proposed. The importance of the immune system for the control and/or prognosis of CRC is suggested by the correlation between infiltration of lymphocytes and good prognosis/prolonged survival.

Cancer related immunosuppression is often associated with a systemic, chronic inflammation with increased pathological production of several cytokines, wherein cytokines are chemical mediators released by cells that affect the behaviour of other cells, (eg. IL-1βS, IL-1Ra IL-6, IL-10, IL-17, TNF-α, $PGE_2$, TGF-β). IL-6, and TNF-α are involved in a paraneoplastic syndrome frequently found in cancer patients. This syndrome is characterized by a poor performance status, low-grade fever, anorexia, weight-loss, fatigue and distortion of various biochemical laboratory parameters. This condition is said to correlate to the tumour burden of the patient, being worse in more advanced disease. In particular, IL-6, a pleiotropic, proinflammatory cytokine, is of importance for the regulation of immune reactivity (Lotz: 1995. Cancer Treat Res 80:209; Barton B E. 1996. Med Res Rev 16:87). In addition to its regulatory role in immune and inflammatory responses, it regulates hepatic acute-phase protein synthesis, hematopoiesis and bone metabolism. IL-6 production can be induced by a large variety of stimuli which includes;

- Other cytokines (such as IL-1β, IL-17 and TNF-α)
- Microbial products (such as endotoxins, e.g. lipopolysaccharide from Gram-negative bacteria like *Escherichia coli*, formalin fixed or dried *Staphylococcus aureus*, mycobacterial cell wall components or synthetic constructs thereof (muramyl dipeptide) and *Staphylococcus aureus* anterotixins A (SEA) and B (SEB)
- Mitogens, such as Phytohemagglutinin (PHA) and Concanavalin A (ConA)
- Plasma/serum factors, such as IgG, IgA, immunocomplexes and fibrinogen or fibrin degradation products, e.g. D-dimer
- Complement factors, such as C3a and C5a
- Acute-phase reactants, such as C-reactive protein (CRP)
- Extracellular matrix (ECM) components, such as fibronectin, vitronectin or proteolytic fragments or synthetic peptides thereof
- Neuropeptides In addition, other pro-inflammatory cytokines (TNF-α, IL-1 and IL-8) can be induced in mononuclear cells by P-selectin (from platelets), free hemoglobin and soluble CD23. An increased serum concentration of IL-6 is often found in cancer patients, especially in patients with advanced disease and has been reported to correlate with a poor prognosis in various types of cancer, e.g. multiple myeloma, chronic lymphocytic leukemia, renal cell carcinoma, prostate cancer, ovarian cancer, metastatic breast cancer, pancreatic carcinoma and colorectal cancer. IL-6 may also be involved in the malignant process as an autocrine or paracrine growth factor in cancers like renal cell carcinoma, multiple myeloma, prostate cancer, colon cancer and Kaposi's sarcoma. Except for a possible prognostic value, the information provided by determination of serum concentrations of factors such as IL-6 can, can be questioned. The cellular origin of these serum factors is often unknown, they are immensely diluted in serum and their half-life is not accounted for. The information obtained from serum determinations of such factors is therefore most likely just a faint reflection of the mechanisms behind their appearance in serum.

An increased systemic concentration of IL-6 has been reported to correlate with a poor response to chemotherapy and it is well documented that patients with increased IL-6 and/or CRP serum levels cannot be successfully treated with immunotherapy.

The source of serum IL-6 in cancer patients is still somewhat unclear. Although IL-6 can be produced by a broad range of normal cells such as fibroblasts, monocytes, T lymphocytes, endothelial cells and keratinocytes it is generally assumed to be derived from the tumour as it may be produced by certain malignant cells. In a study of 12 colon cancer patients, IL-6 mRNA was expressed in tumour tissue in 83% of the cases but only in one patient in normal mucosa (Piancatelli et al. 1999. J Immunother 22:25) and in another study by Kinoshita et al. it was shown that the IL-6 concentration in tumour tissue of colorectal carcinoma patients were significantly higher than in normal mucosa and was correlated with the serum IL-6 concentration. In addition, serum level of IL-6 was correlated with such parameters as tumour size and proliferative activity of the tumour (Kinoshita et al. 1999 Cancer 85:2526)

Based on these observations IL-6 was chosen as an interesting parameter of dysregulation of the immune system in cancer patients. In the present study LPS-induced IL-6 production by blood cells from CRC patients was determined preoperatively and a possible correlation to the prognosis of these patients was analysed.

SUMMARY OF THE PRESENT INVENTION

The object of the present invention is to obtain a possibility of diagnosing a possible recurrence of a cancer after resection of a primary tumour. Such a diagnosis is of utmost importance to;

a) provide a patient having a prognosis of low recurrence probability with adequate information and adequate follow up routines, which will save considerable health care costs, and;
b) provide a patient with a high risk of recurrence with the utterly best care to prevent recurrence.

The importance of the systemic immune status for control of tumours is further demonstrated by the prognostic value of endotoxin lipopolysaccharide induced production of interleukin-6 by peripheral blood mononuclear cells, PBMCs, from cancer patients.

The invention will be described below with reference to the determination of a serum factor, which in cooperation with a cytokine stimulating factor enables prognosis of the outcome of future cancer recurrence, if any, as well as the diagnosis of possible recurrence of colon cancer, however, without being restricted thereto.

DETAILED DESCRIPTION OF THE PRESENT INVENTION

The present invention relates in particular to a method for determination of a serum factor in cancer patient sera, said factor acts synergistically with a cytokine stimulating factor to enhance cytokine production by indicator cells in cell cultures in the presence of cancer patient serum, whereby said serum factor is identified by production of the cytokine IL-6 in the presence of a cytokine stimulating factor, whereby the indicator cells are mononuclear blood cells or a cell line.

In a preferred embodiment the cytokine stimulating factor is from the group comprising microbial products, mitogens, plasma/serum factors, Extra cellular matrix molecules, cytokines, acute-phase reactants, complement factors or neuropeptides.

In a preferred embodiment the microbial product is an endotoxin.

In a preferred embodiment the endotoxin is a lipopolysaccharide.

A further aspect of the invention relates to a method for determining risk of recurrence of cancer after resection of the primary tumour, whereby indicator cells in the form of mononuclear blood cells or a cell line in a cell culture comprising lipopolysaccharide in a concentration of below 0.10 ng/ml produces a significant amount of IL-6.

In a preferred embodiment the blood cells are peripheral blood mononuclear cells.

In a preferred embodiment the cytokine determined is a chemical mediator affecting the behaviour of other cells.

In a preferred embodiment the cytokine determined is one or more from the group of cytokines comprising IL-1β, IL-1Ra IL-6, IL-10, IL-17, TNF-α, $PGE_2$, TGF-β.

In a preferred embodiment the cytokine is interleukin-6 (IL-6).

In a preferred embodiment the peripheral blood mononuclear cells are cultivated in the presence of up to 50 pg/ml of lipopolysaccharide.

In a preferred embodiment the endotoxin lipopolysaccharide is derived from *Escherichia coli* 026:B6.

In a preferred embodiment the cultivation of the peripheral blood mononuclear cells takes place in a medium consisting of RPMI 1640 comprising 1% human serum albumin (HSA), and supplemented with penicillin, streptomycin, L-glutamine and said medium further consisting of 10% fresh, heat-inactivated serum.

In a preferred embodiment the cytokine production is determined by immunoassays, such as ELISA, ELISpot, RIA, any blotting technique, including Western blotting, Southern blotting, any bioassay, any tissue culture technique, RT-PCR, flow cytometry, cytometric bead array, DNA microarray and/or proteomics.

Materials and Methods
Patients

Thirty-five patients with colorectal cancer were tested before radical resection of the primary tumour. Thus, only patients with stage I-III were included in this study and stage IV patients with distant metastases were excluded. LPS induced production of interleukin-6 by patient PBMCs cultured for 24 hours in autologous serum was analysed by a standard ELISA-technique. All patients were then followed for at least 46 months.

Serum

Sera, collected from healthy volunteers or from patients with colorectal carcinoma, was heat-inactivated at 56° C. for 30 minutes. Fresh sera was used for cell cultures (see below), whereas aliquots of the same sera were saved at −70° C. for determination of IL-6 concentrations.

Isolation of Peripheral Blood Mononuclear Cells (PBMC)

A blood sample was collected from healthy volunteers or from colorectal carcinoma patients preoperatively on the same day as surgery was performed. Venous blood was drawn in glass vacuum tubes with acid dextrose citrate solution A as anti-coagulant (Vacutainer, Becton Dickinson, Franklin Lakes, N.J.). Erythrocytes were removed by sedimentation on 2% dextran T500 solution (Amersham Pharmacia Biotech AB, Uppsala, Sweden) in 0.9% NaCl. Mononuclear cells (PBMC) were then isolated by Ficoll-paque Plus (Pharmacia, Uppsala, Sweden) density gradient centrifugation after which the cells were washed twice in RPMI 1640 Dutch's modification (Gibco BRL, Life Technologies, Paisley, Scotland) with 2% human serum albumin (HSA, Pharmacia & Upjohn, Stockholm, Sweden) (RPMI/2% HSA). Cell viability was assessed by exclusion of 0.05% Trypan Blue and was always above 95%. The cell suspension was stained with Türk's solution and the number of lymphocytes and monocytes in the PBMC preparation were counted in a hemocytometer. PBMCs were resuspended in RPMI/2% HSA and the cell concentration adjusted to $5 \times 10^5$ lymphocytes/ml.

Culture of PBMCs for the Generation of Cell Culture Supernatants

PBMC were cultured in round-bottomed, tissue culture microtitre plates (Costar 3799, Corning Inc, Corning, N.Y.). 100 µl per well of culture medium consisting of RPMI 1640 supplemented with 200 IU/ml Penicillin, 200 µg/ml Streptomycin, 4 mM L-glutamine (all from Sigma Chemical Company, St. Louis, Mo.) and 20% fresh, heat-inactivated serum was then added to the microtiter plates followed by 100 µl per well of cell suspension in RPMI/2% HSA. Hence, the final concentration per well is 50,000 PBMCs, 10% serum and 1% HSA. Lipopolysaccharide from *Escherichia coli* 026:B6 (LPS, Sigma Chemical Co) was also added at a final concentration of 0.05 ng/ml. The cells were cultured in a humidified 5% $CO_2$ atmosphere at 37° C. Supernatants (SN) were harvested after 24 hours and residual cells removed by centrifugation in a refrigerated centrifuge at 2600 G for 5 minutes. SN were frozen and stored at −70° C. until IL-6 concentrations were evaluated by ELISA.

Analysis of Cytokines

Cytokine production can be determined by immunoassays, such as ELISA, ELISpot, RIA, any blotting technique, including Western blotting, Southern blotting, any bioassay, any tissue culture technique, RT-PCR, flow cytometry, cytometric bead array, DNA microarray and/or proteomics.

IL-6 in cell culture SN or in serum was measured by ELISA using the DuoSet⁰ ELISA development kit or Quantikine ELISA kit for human IL-6 (R&D Systems Europe, Ltd., Abingdon, UK) following the manufacturer's recommended procedures. The lower limit of detection was 3.1 pg/ml. All samples were analysed as duplicates. Both SN and sera had been kept frozen at −70° C. before determination of IL-6.

Results

Spontaneous and LPS-induced production of IL-6 in purified PBMCs in vitro

In the present investigation we analyzed spontaneous and LPS-induced production of IL-6 by purified PBMCs in vitro. In setting up in vitro culture models, there is always the risk that the regulatory mechanisms operating in vivo are changed or completely lost. In order to avoid this, the mononuclear blood cells were manipulated as little as possible, thus no attempts were made to further purify monocyte or lymphocyte subsets, especially as their interaction might be crucial to maintain the in vivo regulation of cytokine production. Many studies investigating cytokine production by PBMCs from cancer patients have used fetal calf serum rather than autologous serum in the culture medium. This is advantageous from the point of standardizing the culture conditions, but it may introduce new unknown factors in the culture model and cancer related autologous, possibly immune regulatory serum factors are removed. Thus, all cultures in the present investigation used autologous sera in the culture medium.

PBMCs were isolated from forty patients with colorectal cancer (CRC) preoperatively and were analysed for spontaneous and for LPS-induced IL-6 production in short term cultures with autologous sera in the culture medium. Five of these patients had synchronous metastases and are therefore excluded from the following analyses. Patient characteristics are: 11 patients had T1-2, 21 patients had T3 and 3 patients had T4 tumours; 21 patients were N0, 10 patients were N1 and 4 patients were N2; five patients had distant metastases.

Under these culture conditions the spontaneous IL-6 production by PBMCs was very low in both cancer patients (mean 221±48, range 31-1120) and controls (mean 162±52, range 20-1620) and was detectable in 9 out of 40 patients and 12 out of 35 controls PBMCs were stimulated with LPS at a low concentration in order to find out if PBMCs from cancer patients are influenced by the malignant disease in a way, which allows discrimination between patients with different prognosis. In order to make the in vitro model as sensitive as possible only a low dose of LPS was used. The use of LPS-stimulation in culture models, where the intention is to obtain data of prognostic value, has to be interpreted with great care as some 10 percent of the population carries a mutation resulting in no response to LPS. After LPS stimulation, analysis showed that PBMCs from CRC patients produced more IL-6 (mean 7085+1510, range 31-32400) than PBMCs from healthy controls (mean 3899+779, range 57-24000), p=0.065 (FIG. 1). An analysis of the distribution of IL-6 producers among healthy controls and cancer patients showed that a production of 5000 pg/ml discriminated between two groups, which in the following analysis are called low and high producers. Spontaneous IL-6 production was at most 15% of LPS-stimulated IL-6 production in high producers.

No significant difference in IL-6 production by PBMCs due to stage, occurrence of lymph node metastases, degree of differentiation or to the presence or absence of vascular invasion in the tumour tissue was found. There was a slight tendency towards a higher IL-6 production by PBMCs from patients with left sided tumours as compared to right sided (p=0.22) and PBMCs from the few patients (N=3) with T4 tumours had a significantly higher IL-6 production than those from T2 or T3 tumours (p<0.0001).

Figure 2:
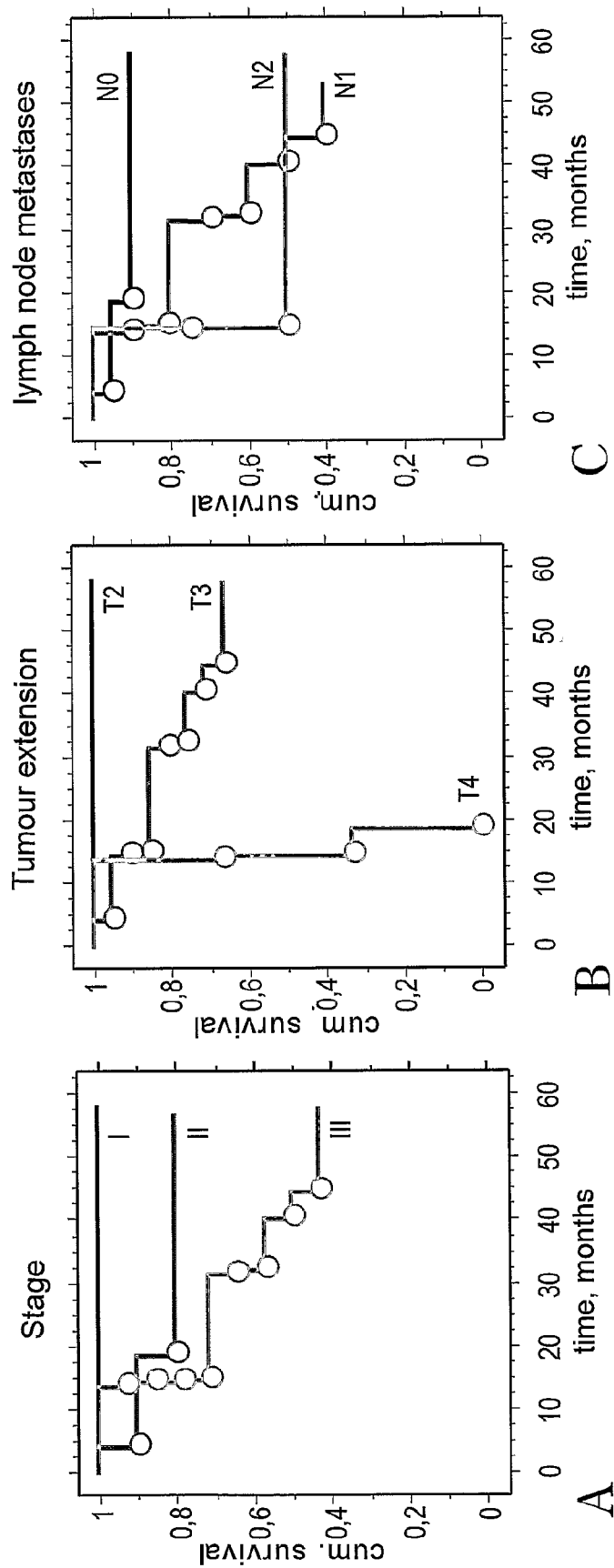

For comparison with results in the following analyses the effect of tumour stage, tumour extension and lymph node metastases is shown in FIG. 2. These results are in very good agreement with previously published data.

As shown, in the majority of patients the spontaneous production was low, which might be due to the sensitivity of the method used. However, from these results it cannot be excluded that the low serum concentration often found in cancer patient sera actually is derived from PBMCs. Interestingly, LPS-induced IL-6 production was in general higher in cultures from cancer patients as compared to cultures from healthy controls, which shows that PBMCs from cancer patients are somehow induced to produce IL-6. In contrast to studies showing an increased serum concentration of IL-6, we can, based on the present results, claim that the increased LPS-induced IL-6 production is due to cancer related modulation of the immune system.

Correlation Between the Overall Survival of CRC Patients and IL-6 Production

Next a possible correlation between the overall survival of CRC patients and IL-6 production by their PBMCs was analysed.

The median follow-up time was 52.8 months and all patients were followed for at least 46 months. When only patients with radical resection were analysed together, low-producers of IL-6 had a significantly better survival compared to high producers (FIG. 3A). All 21 patients with low production of IL-6 were still alive at 46 months following primary surgery, but 10 out of 14 with high production had died, p<0.0001. The median survival was not reached in the former group but was 31 months for high-producers.

Two patients in the group of 21 with low LPS-induced IL-6 production had intra-abdominal recurrences, one a regional recurrence after 58 months and the other retroperitoneal lymph node metastases after 30 months. This is hardly surprising, as the test used in the present investigation obviously does not correlate with the local aggressiveness of the tumour, shown as vessel invasion or lymph node metastases. However, the over all survival was significantly better for low-producers of IL-6. This indicates that the production of cancer related factors supporting LPS induced IL-6 production does not correlate to the local aggressiveness of the tumour, but rather to its propensity to establish distant metastases. Alternatively, there might be a regional-systemic gradient of these cancer related factors modulating the immune function so that the regional tumour control is broken down while systemic protection still is active (North R. 1985. Advances in Cancer Res 45:1). It is interesting to note that PBMCs from the patient, who had lymph node metastases after 30 months, did not at all respond to LPS. He might, thus carry the mutation discussed above and can therefore not be identified using the present prognostic test.

In the group of patients with lymph node metastases, IL-6 production identified those with a poor prognosis. As shown in FIG. 3B, all patients, in total six patients having low IL-6 production were alive, whereas none out of 8 having high production of IL-6 was alive after 46 months. Similarly, patients with T3 tumours and low IL-6 production had a significantly better survival than high producers. All 12 patients in the former group were alive compared to 2 out of 9 with high IL-6 production. Even in the subset of T3/N12 patients, low IL-6 production predicts a long term event free survival (6 out of 6 patients) whereas all of the patients with high production have died (6 out of 6). Thus, low IL-6 production by PBMCs from colorectal cancer patients predicts long term event free survival after radical resection of the primary tumour. A multivariate Cox regression analysis, stratified for T- and N-stage identified IL-6 production as an independent prognostic factor.

Influence of Serum Factors on LPS Induced Production of IL-6

To further explore the influence of serum factors on LPS induced production of IL-6, PBMCs from AB0-compatible healthy blood donors were cultured in cancer patient sera (Table 1).

TABLE 1

The effect of cancer patient sera on LPS induced IL-6 production (pg/ml) by PBMCs from healthy controls. Each cancer patient serum was tested on control cells from two persons. When cancer patient sera had the same effect in the two tests, the result was considered to be conclusive, either stimulatory or inhibitory.

| Patient | Cancer patients autologous sera | Controls autologous sera | Control cells cancer pat. sera | Cancer patient serum factor |
|---------|----|-------|-------|-------------|
| 1 | 5501 | 205 | 2622 | stimulatory |
|   |      | 220 | 2309 | stimulatory |
| 2 | 525  | 772 | 49   | inhibitory  |
|   |      | 1104| 64   | inhibitory  |
| 3 | 2586 | 105 | 1337 | stimulatory |
|   |      | 548 | 2386 | stimulatory |
| 4 | 3023 | 623 | 251  | inhibitory  |
|   |      | 602 | 184  | inhibitory  |
| 5 | 336  | 300 | 1540 | stimulatory |
|   |      | 512 | 3800 | stimulatory |
| 6 | 7544 | 820 | 6374 | stimulatory |
|   |      | 12349| 19208| stimulatory|
| 7 | 1365 | 1440| 1318 | uncertain   |
|   |      | 4746| 2681 | uncertain   |
| 8 | 845  | 698 | 1195 | uncertain   |
|   |      | 2283| 823  | uncertain   |
| 9 | 171  | 1306| 320  | inhibitory  |
|   |      | 474 | 111  | inhibitory  |

As shown in Table 1 the results were inconclusive in two out of nine experiments, four cancer patient sera had a marked stimulatory activity and in three there seems to be some inhibitory activity. The possibility to analyse the role of cellular factors in PBMCs from cancer patients is complicated by the fact that these cells have been in an in vivo milieu for quite some time where they have been triggered by serum factors modulating their reactivity to LPS. Therefore these analyses were not performed. However, it can be concluded that serum factors are of importance for LPS induced IL-6 production by PBMCs.

Further in the present test method, high and low producers of IL-6 (cancer and control persons) after LPS stimulation were identified in autologous short-term cultures of PBMCs. As shown in Table 1, the enhanced IL-6 production can be transferred by serum factors. In order to investigate the possibility that these serum factors can be used to discriminate between high and low producers of IL-6 after LPS stimulation, sera were used in the culture medium of cultures with new indicator cells (PBMCs from healthy controls). The LPS induced IL-6 production in these cultures was then determined and the amount of IL-6 produced was compared to the amount produced in autologous cultures with these sera.

There is a highly significant correlation between the results from the autologous cultures and the cultures where sera were cultured together with new indicator cells. This was the case both when sera from cancer patients and healthy controls were analysed.

Provided that the majority of malignant tumours are recognized as non self by the immune system, a proper analysis of the tumour-host interaction should provide information of prognostic value. In fact, as shown in the present investigation, the immune system obviously plays a very important role at an early stage of cancer and the determination of the immune regulatory mechanisms can be used to develop good prognostic parameters. The stage of cancer diseases, based on local aggressiveness and metastatic potential, provides important prognostic information. The stage of a tumour can be the result of the intrinsic biological properties of the tumour cells or the result of interplay between these properties and the host defense mechanisms, provided that these mechanisms are efficient enough to influence tumour progression. Indeed, recent data from both mouse and human studies provide strong support for the concept of cancer immunosurveillance and suggest that tumour development is the result of immune system-tumour interactions. Our results demonstrate that immune regulatory mechanisms, determined as LPS-induced IL-6 production, play a major role for the prognosis of CRC. The stage of cancer can thus, at least to a large extent, be considered the result of the efficacy of the immune system. Based on the present data on LPS-induced IL-6 production, cancer patients as well as healthy controls can be divided into two groups, low-producers and high-producers with a production of less than 5000 pg/ml or more. That a large number of cancer patients were low-producers is, however, not surprising as a very good correlation was found between high LPS-induced IL-6 production and a poor prognosis. It is then reasonable to assume that a high LPS-induced IL-6 production is somehow involved in a poor protection against systemic dissemination of the tumour cells. As also PBMCs from some healthy controls showed an increased LPS-induced production of L-6, this phenomenon can be a part of normal immune regulation possibly occurring during a short period when the activity of the immune system is down-regulated after activation due to infections or inflammatory processes. In cancer patients this type of down-regulation is dangerous, because the inflammatory reaction is due to the presence of a malignant tumour, which sustains long-lasting down-regulatory mechanisms.

It can thus be concluded that malignant tumours already before resection of the primary tumour influence the immune system and that this system plays a major role in the control of malignant tumours. Furthermore, tests based on these immune regulatory mechanisms can provide important prognostic information.

FIGURE LEGENDS

FIG. 1. LPS induced IL-6 production in short term cultures of PBMCs from colorectal cancer patients (n=35) and healthy controls (n=35). Each bar represents one patient/control. Tests are sorted according to IL-6 production.

FIG. 2. Kaplan-Meyer cumulative survival plots. A. According to stage, I (■) (blue), II (green) and III (■) (red); B According to tumour extension, T2 (■) (blue), T3 (green) and T4 (■)(red). C. According to lymph node metastases, N0 (■) (blue), N1 (green) and N2 (■)(red).

Figure 3:
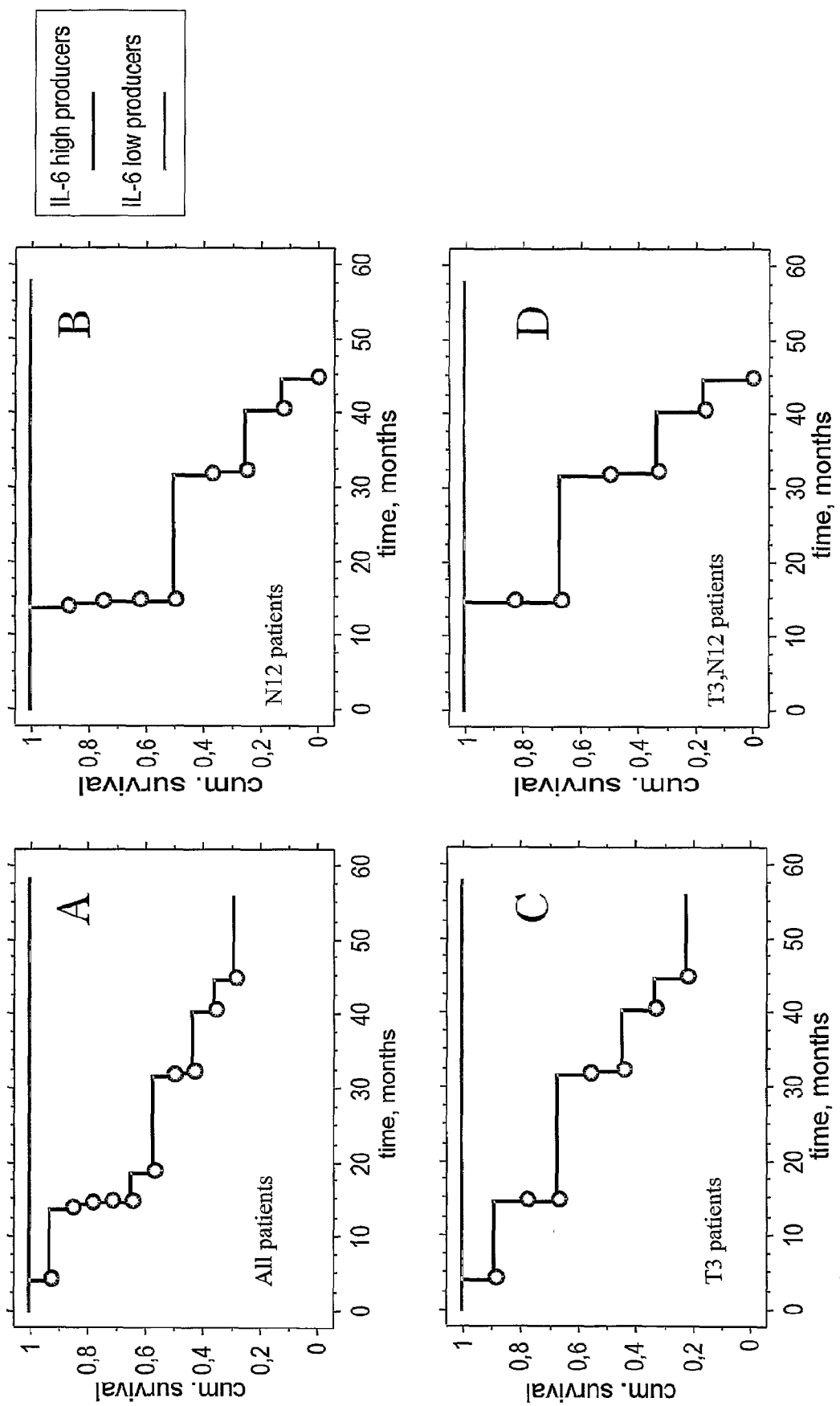

FIG. 3. IL-6 production in radically resected colorectal cancer patients. Kaplan-Meyer cumulative survival plots. A. All patients; B. Patients with lymph node metastases (N12); C. Patients with T3 tumours; D. Patients with T3, N12 tumours. IL-6 low producers (green), high producers (■) (blue).

The invention claimed is:

1. A method for identifying a prognosis for survival of a patient with colorectal cancer and lymph node metastases comprising:

(a) contacting a suspension of peripheral blood mononuclear cells (PBMCs) and human sera from said patient with lipopolysaccharide;
(b) measuring the amount of interleukin-6 (IL-6) in the suspension of (a); and
(c) classifying said patient as having a reduced prognosis for survival when the amount of IL-6 measured in the suspension of (a) is above the amount of IL-6 in a suspension of lipopolysaccharide, and PBMCs and sera from a human with colorectal cancer and a good prognosis for survival; or
(d) classifying said patient as having an increased prognosis for survival when the amount of IL-6 measured in the mixture of (a) is equivalent to the amount of IL-6 in a suspension of lipopolysaccharide, and PBMCs and sera from a human with colorectal cancer and a good prognosis for survival.

2. The method of claim 1, wherein said patient has had a primary tumor removed.

3. The method of claim 1, wherein the amount of IL-6 is measured by an immunoassay, a blotting technique, ELISA, ELISpot, flow cytometry, cytometric bead array, or proteomics.

4. The method of claim 3, wherein the immunoassay is ELISA or flow cytometry.

5. A method for identifying a prognosis for survival of a patient with local advanced colorectal cancer tumors comprising:
(a) mixing lipopolysaccharide with peripheral blood mononuclear cells (PBMCs) and human sera from said patient;
(b) measuring the amount of interleukin-6 (IL-6) in the mixture of (a); and
(c) classifying said patient as having a reduced prognosis for survival when the amount of IL-6 measured in the mixture of (a) is above the amount of IL-6 in a suspension comprising lipopolysaccharide, and PBMCs and sera from a human that has colorectal cancer and a good prognosis for survival; or
(d) classifying said patient as having an increased prognosis for survival when the amount of IL-6 measured in the suspension of (a) is equivalent to the amount of IL-6 in a suspension comprising lipopolysaccharide, and PBMCs and sera from a human that has colorectal cancer and a good prognosis for survival.

6. The method of claim 5, wherein the patient with local advanced tumors comprises at least T3 stage colorectal cancer.

7. The method of claim 5, wherein said patient has lymph node metastases.

* * * * *